United States Patent
Kalinovich et al.

(10) Patent No.: US 9,905,885 B2
(45) Date of Patent: Feb. 27, 2018

(54) 1,2,4-THIADIAZINANE-3,5-DIONE-1,1-DIOXIDE DERIVATIVES, PRODUCTION AND USE THEREOF

(71) Applicants: JACOBS UNIVERSITY BREMEN GGMBH, Bremen (DE); WESTFAELISCHE WILHELMS-UNIVERSITAET MUENSTER, Muenster (DE)

(72) Inventors: Nataliya Kalinovich, Bremen (DE); Gerd-Volker Roeschenthaler, Bremen (DE); Tanja Schedlbauer, Meunster (DE); Johannes Kasnatscheew, Duelmen (DE); Katja Vlasov, Mannheim (DE); René Schmitz, Mannheim (DE); Raphael Wilhelm Schmitz, Muenster (DE); Romek Ansgar Mueller, Ingolstadt (DE); Martin Winter, Muenster (DE); Stefano Passerini, Ulm (DE)

(73) Assignees: JACOBS UNIVERSITY BREMEN GGMBH, Bremen (DE); WESTFAELISCHE WILHELMS-UNIVERSITAET MUENSTER, Muenster (DE)

( * ) Notice: Subject to any disclaimer, the term of this patent is extended or adjusted under 35 U.S.C. 154(b) by 368 days.

(21) Appl. No.: 14/409,472

(22) PCT Filed: Apr. 25, 2013

(86) PCT No.: PCT/DE2013/100153
§ 371 (c)(1),
(2) Date: Dec. 19, 2014

(87) PCT Pub. No.: WO2013/189481
PCT Pub. Date: Dec. 27, 2013

(65) Prior Publication Data
US 2015/0188191 A1    Jul. 2, 2015

(30) Foreign Application Priority Data
Jun. 20, 2012  (DE) .................. 10 2012 105 377

(51) Int. Cl.
*H01M 6/16*        (2006.01)
*H01M 10/0567*     (2010.01)
*C07D 285/18*      (2006.01)
*H01M 10/052*      (2010.01)
*H01M 10/0569*     (2010.01)
*H01M 10/0525*     (2010.01)
*H01M 10/0566*     (2010.01)

(52) U.S. Cl.
CPC ...... *H01M 10/0567* (2013.01); *C07D 285/18* (2013.01); *H01M 10/052* (2013.01); *H01M 10/0569* (2013.01); *H01M 10/0525* (2013.01); *H01M 10/0566* (2013.01); *H01M 2300/0025* (2013.01); *H01M 2300/0028* (2013.01)

(58) Field of Classification Search
CPC ........ H01M 6/16; H01M 6/162; H01M 6/168; H01M 10/0564; H01M 10/0567
See application file for complete search history.

(56) References Cited

U.S. PATENT DOCUMENTS

| | | | |
|---|---|---|---|
| 2,466,396 A | 4/1949 | Dickey | |
| 2011/0206979 A1 | 8/2011 | Giroud et al. | |
| 2014/0017559 A1* | 1/2014 | Kawasaki | H01M 4/364 429/200 |

FOREIGN PATENT DOCUMENTS

KR    10 2009 0 053 469 A    5/2009

OTHER PUBLICATIONS

R. L. Hinman et al.: "The 1,2,4-Thiadiazine Ring System. III. The Dissociation of 1,2,4,2H-Thiadiazine-3,5(4H,6H)-dione 1,1-Dioxide", The Journal of Organic Chemistry, vol. 26, No. 9, pp. 3461-3467 (1961).
R. L. Hinman et al.: "The 1,2,4-Thiadiazine Ring System. I. The Synthesis of 1,2,4,2H-Thiadiazine-3,5(4H,6H)-dione 1,1-dioxide", Journal Am. Chem. Soc., vol. 81, No. 21, pp. 5655-5658 (1959).
B. E. Hoogenboom et al.: "Chemistry of the 1,2,4-Thiadiazine Ring System. II. A New Synthesis of 1,2,4,2H-Thiadiazine-3,5(4H,6H)-dione 1,1-dioxide", The Journal of Organic Chemistry, vol. 24, No. 12, pp. 1983-1986 (1959).

* cited by examiner

*Primary Examiner* — Ula C Ruddock
*Assistant Examiner* — Julian Anthony
(74) *Attorney, Agent, or Firm* — Norman B. Thot

(57) ABSTRACT

The present invention provides a compound with a general formula (I)

$$
\begin{array}{c}
\text{(I)}
\end{array}
$$

or a salt thereof, wherein $R^1$ and $R^2$, are, independently of each other, F or $C_nF_{2n+1}$ with n=1-10, and $R^3$ and $R^4$ are, independently of each other, $C_1$-$C_{10}$-alkyl.

21 Claims, No Drawings

1,2,4-THIADIAZINANE-3,5-DIONE-1,1-DIOXIDE DERIVATIVES, PRODUCTION AND USE THEREOF

CROSS REFERENCE TO PRIOR APPLICATIONS

This application is a U.S. National Phase application under 35 U.S.C. § 371 of International Application No. PCT/DE2013/100153, filed on Apr. 25, 2013 and which claims benefit to German Patent Application No. 10 2012 105 377.4, filed on Jun. 20, 2012. The International Application was published in German on Dec. 27, 2013 as WO 2013/189481 A1 under PCT Article 21(2).

FIELD

The present invention relates to 1,2,4-thiadiazinane-3,5-dione-1,1-dioxide derivatives, to their use, and to a method for their production. The present invention also relates to an electrolyte, more specifically, an electrolyte for lithium-ion primary batteries and lithium-ion secondary batteries, comprising 1,2,4-thiadiazinane-1,1-dioxide-derivatives, to primary batteries or secondary batteries with such an electrolyte, and to electric appliances or electric vehicles with such primary batteries or secondary batteries.

1,2,4-thiadiazinane-3,5-dione-1,1-dioxide as well as methods for its production are described in Hinman, R. L., and Locatell Jr., L. (1959), J. Am. Chem. Soc. 81 (21), 5655-5658, and in Hoogenboom, B. E., et al. (1959), J. Org. Chem. 24 (12), 1983-1986.

Powerful primary batteries and secondary batteries are increasingly needed for many applications, for example, to operate portable electronic devices such as mobile phones and the like, but also for electric vehicles. The requirements imposed on such primary batteries and secondary batteries are increasingly high, for example, with regard to their capacity, safety, capacity losses and aging properties. This concerns in particular lithium-ion secondary batteries which have prevailed in the field of consumer electronics and electric vehicles.

SUMMARY

An aspect of the present invention is to further improve primary batteries and secondary batteries, more specifically, lithium-ion primary batteries and secondary batteries.

In an embodiment, the present invention provides a compound with a general formula (I)

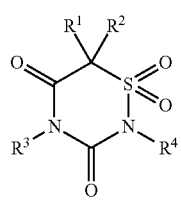

or a salt thereof, wherein $R^1$ and $R^2$, are, independently of each other, F or $C_nF_{2n+1}$ with n=1-10, and $R^3$ and $R^4$ are, independently of each other, $C_1$-$C_{10}$-alkyl. The compound of the present invention is suitable as an electrolyte additive for lithium-ion primary batteries and secondary batteries. The present invention also provides a method for production of the compound and an electrolyte for lithium-ion primary batteries and secondary batteries.

DETAILED DESCRIPTION

In an embodiment, the present invention provides a compound with the general formula (I)

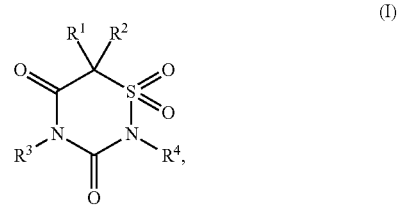

or a salt thereof, wherein $R^1$ and $R^2$, are, independently of each other, F or $C_nF_{2n+1}$ with n=1-10, and $R^3$ and $R^4$ are, independently of each other, $C_1$-$C_{10}$-alkyl.

The compound of the present invention with the general formula (I) is particularly suitable as an electrolyte additive, more specifically as an additive to an electrolyte for lithium-ion primary batteries or lithium-ion secondary batteries. The compound according to the present invention contributes to the formation of an SEI layer on the negative electrode, for example, a graphite electrode, thus protecting the surface of the electrode. This results in advantages for lithium-ion primary batteries/secondary batteries, for example, with regard to an improved thermal stability, less capacity losses and less ageing. It is assumed that the compound according to the present invention breaks down on the negative electrode during the first charging and discharging cycle and forms an advantageous boundary layer.

Unless explicitly stated otherwise, or unless the context distinctly indicates otherwise, the term "compound according to the present invention" refers herein to the compound according to the formula (I) in the form of a free compound or in the form of its salts.

The term "primary battery" herein refers to a non-rechargeable storage system for electric energy based on an electrochemical system (primary cell), whereas a "secondary battery" refers to a rechargeable storage system for electric energy based an electrochemical system (secondary cell). A "lithium-ion secondary battery" or "li-ion secondary battery" is to be understood as a secondary battery based on the use of lithium (Li). Examples thereof are lithium-titanate secondary batteries, lithium-air secondary batteries, lithium-manganese secondary batteries, lithium iron phosphate secondary batteries, lithium iron manganese phosphate secondary batteries, lithium iron yttrium phosphate secondary batteries, lithium-sulphur secondary batteries, lithium nickel cobalt manganese oxide secondary batteries, lithium nickel cobalt aluminum oxide secondary batteries, lithium polymer secondary batteries, and tin sulphur secondary batteries. A lithium secondary battery customarily has a negative and a positive electrode, wherein lithium-ions can travel back and forth between the two electrodes through an electrolyte during charging or discharging. The negative electrode is often substantially composed of graphite, whereas the positive electrode customarily has lithium-transition metal compounds, e.g., lithium transition metal oxides. Examples of lithium transition metals include e.g., lithium iron phosphate (LFP) or lithium transition metal oxides such as lithium cobalt dioxide, lithium nickel dioxide, lithium nickel cobalt manganese oxide, or lithium nickel cobalt aluminum oxide. Instead of graphite, other alloy-forming substances, e.g., silicium, aluminum, and tin may be used.

The term "SEI layer" (SEI=Solid Electrolyte Interphase) refers to an electrode cover layer that is permeable to lithium-ions but largely impermeable to solvent molecules of the electrolyte and which protects the negative electrode, e.g., a graphite electrode, of a li-ion secondary battery by preventing the intercalation of solvent molecules or solvated lithium-ions and/or protects the electrolyte against reductive breakdown on the negative electrode.

An "electrolyte" herein refers to a solution of at least one conducting salt in a suitable solvent or an ionic liquid. Suitable solvents are, for example, anhydrous aprotic solvents. Lithium hexafluorophosphate dissolved in ethylene carbonate is an example of an electrolyte.

The term "SEI-forming electrolyte additive" refers to compounds that are added to an electrolyte and that improve the SEI formation as compared to an electrolyte without the additive.

The term "alkyl" includes saturated and unsaturated aliphatic (non-aromatic) groups, including straight-chain alkyl groups (e.g., methyl, ethyl, propyl, butyl, pentyl, hexyl, heptyl and octyl groups) and branched alkyl groups (e.g., isopropyl, tert-Butyl, isobutyl groups). The term "$C_1$-$C_{10}$-alkyl" means an alkyl group with 1, 2, 3, 4, 5, 6, 7, 8, 9 or 10 C-atoms.

$R^1$ and $R^2$ are, independently of each other, F or $C_nF_{2n+1}$, wherein n is 1-10, i.e., 1, 2, 3, 4, 5, 6, 7, 8, 9 or 10. $R^1$ and/or $R^2$ can, for example, be $CF_3$ (n=1), $C_2F_5$ (n=2), $C_3F_7$ (n=3), or $C_4F_9$ (n=4). $R^1$ can, for example, be F or $CF_3$ and $R^2$ is F.

$R^3$ and $R^4$ can, for example, independently of each other, be methyl or ethyl. $R^3$ and $R^4$ can, for example, both be methyl.

In an embodiment, the present invention relates to a method for production of a compound with the general formula (I)

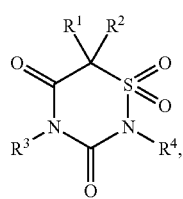
(I)

or of a salt thereof, wherein $R^1$ and $R^2$, are, independently of each other, F or $C_nF_{2n+1}$ with n=1-10, and $R^3$ and $R^4$ are, independently of each other, $C_1$-$C_{10}$-alkyl, which includes the step of reacting a compound with the general formula (II)

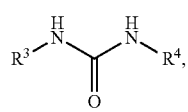
(II)

wherein $R^3$ and $R^4$ are as defined above, with a compound with the general formula (III),

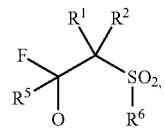
(III)

wherein $R^1$ and $R^2$ are as defined above, and wherein (a) $R^5$ is the O-atom on the same C-atom and $R^6$ is F, or (b) $R^5$ is F and $R^6$ is the O-atom bound to the same C-atom, to which $R^5$ is also bonded.

The method according to the present invention makes it possible to produce the compound according to the present invention with the formula (I) in a relatively simple and efficient manner.

The reaction can, for example, be implemented in a polar basic solvent. Pyridine is an example of a suitable solvent.

In an embodiment of the method according to the present invention, the compound with the general formula (II) can, for example, be reacted with a compound with the general formula (IIIa)

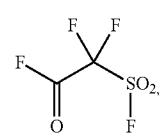
(IIIa)

or a compound with the general formula (IIIb)

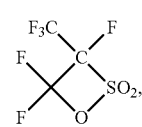
(IIIb)

wherein $R^3$ and $R^4$ can, for example, both be methyl.

The resulting compounds 6,6-difluoro-2,4-dimethyl-1,2,4-thiadiazinane-3,5-dione-1,1-dioxide (Ia) and 6-fluoro-2,4-dimethyl-6-trifluoromethyl-1,2,4-thiadiazinane-3,5-dione-1,1-dioxide (Ib)

Ia

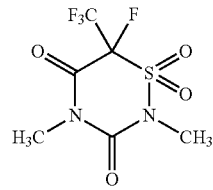
Ib are advantageous with regard to their suitability as SEI-forming electrolyte additives.

In an embodiment, the present invention relates to an electrolyte for a primary battery and/or a secondary battery which comprises a compound of general formula (I).

The compound of general formula (I) can, for example, be present in the electrolyte (a) with a proportion of ≥1.5 weight-%, for example, ≥2.0 weight %, ≥2.5 weight %, ≥3.0 weight % or ≥3.5 weight %, and for example, ≥4.0 weight %, ≥4.5 weight % or ≥5.0 weight %, and/or (b) in a proportion of ≤10.0 weight %, for example, ≤9.0 weight %, ≤8.0 weight %, ≤7.0 weight % or ≤7.5 weight %, for example, ≤6.5 weight %, ≤6.0 weight % or ≤5.5 weight %, relative to the total weight of the electrolyte. The proportion can, for example, lie at approximately 5 weight %.

The electrolyte according to the present invention can, for example, contain an anhydrous aprotic solvent which can, for example, be chosen amongst carbonates, lactones, nitriles, esters, and ethers, and can, for example, be chosen amongst propylene carbonate, ethylene carbonate, diethyl carbonate, dimethyl carbonate, ethyl methyl carbonate, gamma-Butyrolactone, gamma-Valerolactone, adiponitrile, glutaronitrile, acetonitrile, ethyl acetate, tetrahydrofuran, 2-methyltetrahydrofuran, dioxane, and mixtures thereof.

In an embodiment, the electrolyte according to the present invention can, for example, contain propylene carbonate (4-methyl-1,3-dioxolane-2-one), for example, in a proportion of ≥30 weight %, ≥40 weight %, ≥50 weight % and, for example, ≥60 weight %, relative to the total weight of the electrolyte. Using propylene carbonate as a solvent in combination with the compound according to the present invention with the formula (I) has proven to be advantageous. The mixture has a low flash point, for example, thus increasing the safety of the primary battery or the secondary battery.

The electrolyte according to the present invention can, for example, contain a conducting salt, for example, a lithium conducting salt. The conducting salt can, for example, be chosen amongst $LiPF_6$, $LiBF_4$, $LiAsF_6$, $LiSbF_6$, lithium bisoxalatoborate, lithium difluorooxalatoborate, lithium salts of sulfonyl imides, for example, of bis(trifluoromethanesulfonyl)imide and bis(pentafluoroethanesulfonyl)imide, $LiClO_4$, $LiN(SO_2CF_3)_2$, $LiC(SO_2CF_3)_3$, and $LiSO_3CF_3$.

The electrolyte according to the present invention can, for example, be a substantially anhydrous organic liquid electrolyte.

In addition to the compound according to the present invention, the electrolyte according to the present invention can contain other additions, for example, other SEI additives, flame retardants and/or overcharge protection additives. Such additions are known to the person skilled in the art. Examples of flame retardants are organic phosphates, e.g., trimethyl phosphate, triethyl phosphate, triphenyl phosphate, tris(2,2,2-trifluoroethyl)phosphate, bis(2,2,2-trifluoroethyl)methylphosphonate and diphenyl octyl phosphate, alkyl phosphonates, e.g., dimethyl methylphosphonate and dimethyl(2-methyoxyethoxy)methylphosphonate, phosphites, e.g., tris(2,2,2-trifluoroethyl)phosphite and triphenyl phosphite and phosphazene. Examples of overcharge protection additives are metallocene, tetracyanoethylene, tetramethyl phenylenediamine, dihydrophenazine derivatives, for example, dihydrophenazine derivatives, whose nitrogen atoms have been alkyl-substituted, for example, ethyl- or propyl-substituted, wherein the alkyl group may be substituted with OH, if necessary, substituted (hetero)aromates and, if necessary, substituted heterocycles, respectively, in the form of free compounds or in the form of their salts, for example, their alkali metal salts. Other examples of SEI additives are choloroethylene carbonate, fluoroethylene carbonate, vinylene carbonate (VC), vinyl ethylene carbonate (VEC), ethylene sulfite (ES), ethylene sulfate, propane sulfonate, sulfites, e.g., dimethyl sulfite and propylene sulfite, sulfates, if necessary, butyro lactones substituted with F, Cl or Br, phenylethylene carbonates, vinyl acetate and triofluoro propylene carbonates. The electrolyte according to the present invention can, for example, contain only the compound according to the present invention as a SEI additive.

In an embodiment, the present invention relates to the use of a compound having the general formula (I) as an addition to primary battery and/or secondary battery electrolytes, for example, lithium-ion primary battery electrolytes and/or lithium-ion secondary battery electrolytes, for example, lithium-ion primary battery electrolytes and/or lithium-ion secondary battery electrolytes containing propylene carbonate.

In an embodiment, the present invention relates to a primary battery or a secondary battery, a primary battery, or secondary battery pack, which comprise an electrolyte according to the present invention. The primary battery or the secondary battery, the primary battery or secondary battery pack can, for example, be a lithium-ion primary battery, a lithium-ion secondary battery, a lithium-ion primary battery pack or a lithium-ion secondary battery pack. A primary battery or secondary battery pack refers to an arrangement of several primary batteries or secondary batteries which are connected to each other to form a functional unit.

In an embodiment, the present invention relates to an electric appliance or electric vehicle including a primary battery according to the present invention and/or a secondary battery according to the present invention and/or a primary battery pack according to the present invention and/or a secondary battery pack according to the present invention. The electric appliance can, for example, be a portable electric appliance. Examples of portable electric appliances are mobile phones, tablet PCs, notebooks, netbooks, pocket PCs, cordless drill/drivers, portable game consoles, and the like.

The present invention is hereinafter explained in more detail based on examples for illustration purposes.

EXAMPLES

Example 1a—Production of 6,6-difluoro-2,4-dimethyl-1,2,4-thiadiazinane-3,5-dione-1,1-dioxide (compound of general formula (Ia))

6,6-difluoro-2,4-dimethyl-1,2,4-thiadiazinane-3,5-dione-1,1-dioxide according to the general formula (Ia) was produced according to the following general diagram:

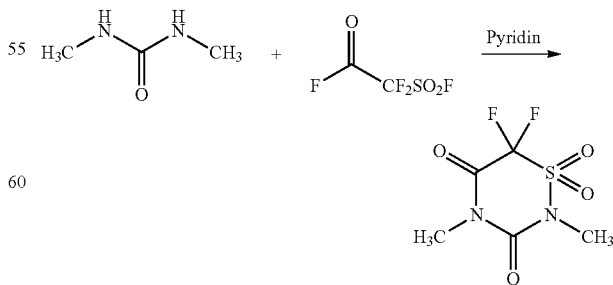

Dimethylurea (13.0 g, 130 mmol) and dry pyridine (16.0 g, 200 mmol) were dissolved in 95 ml of dry $CH_2Cl_2$ in a flask with a Teflon® valve and fluorosulfonyl difluoroacetyl fluoride (compound of general formula (IIIa), 24 g, 130 mmol) was added. The reaction mixture was then agitated for 12 hours at 55° C. After cooling down to room temperature, the mixture was extracted three times, respectively, with 250 ml of saturated NaHCO$_3$ solution. The organic phases were combined, dried with MgSO$_4$, and the product was chromatographed over silica gel (CHCl$_3$/hexane, 5:1).

Yield: 10.0 g, 40% yellow oil $^1$H-NMR (400 MHz, CDCl$_3$): δ=3.33 (s, 3H, CH$_3$), 3.36 (s, 3H, CH$_3$)

$^{19}$F-NMR (400 MHz, CDCl$_3$): δ=−114.5 (s, CF$_2$)

HRMS for [M]$^+$ (C$_5$H$_6$F$_2$N$_2$O$_4$S): reported 228.0016, found 228.0021.

Example 1b—Production of 6-fluoro-2,4-dimethyl-6-trifluoromethyl-1,2,4-thiadiazinane-3,5-dione-1,1-dioxide (compound of general formula (Ib))

6-fluoro-2,4-dimethyl-6-trifluormethyl-1,2,4-thiadiazi-nan-3,5-dion-1,1-dioxide according to the general formula (Ib) was produced according to the following general diagram:

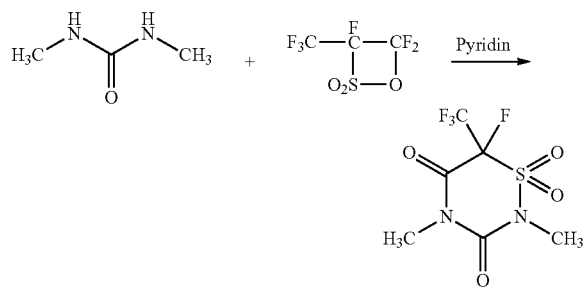

Dimethylurea (6.8 g, 68 mmol) and dry pyridine (12.8 g, 160 mmol) were dissolved in 50 ml of dry CH$_2$Cl$_2$ in a vial with a Teflon® valve and hexafluoropropane sulfone (compound of general formula (IIIb), 16.0 g, 68 mmol) was added. The reaction mixture was then agitated for 12 hours at 55° C. After cooling down to room temperature, the mixture was extracted three times, respectively, with 50 ml of a saturated NaHCO$_3$ solution. The organic phases were combined, dried with MgSO$_4$, and the product was chromatographed over silica gel (CHCl$_3$/hexane, 5:1).

Yield: 10.2 g, 31% orange oil $^1$H-NMR (400 MHz, CDCl$_3$): δ=3.38 (s, 3H, CH$_3$), 3.42 (s, 3H, CH$_3$)

$^{19}$F-NMR (400 MHz, CDCl$_3$): δ=−71.58 (s, 3F, CF$_3$), −166.78 (s, 1F, CF)

Example 2—Examination of a Secondary Battery Cell with an Electrolyte According to the Present Invention A cell with an electrolyte composed of 1 M lithium hexafluorophosphate (LiPF$_6$) with propylene carbonate (PC), which contained 5 weight % of 6,6-difluoro-2,4-dimethyl-1,2,4-thiadiazinane-3,5-dione-1,1-dioxide (compound of general formula (Ia)), relative to the total weight of the electrolyte, was produced and examined. The results show that the embodiment of the electrolyte according to the present invention has very good properties.

An exfoliation of the graphite was completely prevented. The three intercalation steps of the lithium into the graphite were very distinct. The irreversible capacity loss amounted to 200 mAh g$^{-1}$ and the efficiency in the first cycle amounted to 63%.

It was possible to cycle the graphite electrode close to the theoretical capacity of the graphite (372 mAh g$^{-1}$) at 350 mAh g$^{-1}$. A fading could not be observed during cycling. Cycling with an oversized cathode (lithium iron phosphate, LFP) did not result in any problems. The electrolyte was compatible with the cathode material.

The capacity of the graphite electrode remained above 350 mAh g$^{-1}$ up to a C rate (discharge rate) of 5 C. The capacity of the graphite electrode did not drop under 300 mAh g$^{-1}$ even at a C rate of 10 C.

The oxidation stability of the electrolyte was not impaired by the addition of the compound according to the present invention. The insertion of lithium into the cathode material was also improved.

The present invention is not limited to embodiments described herein; reference should be had to the appended claims.

What is claimed is:

1. A compound with the general formula (I)

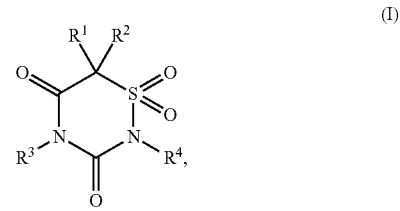

or a salt thereof, wherein,

R$^1$ and R$^2$, are, independently of each other, F or C$_n$F$_{2n+1}$ with n=1-10, and R$^3$ and R$^4$ are, independently of each other, C$_1$-C$_{10}$-alkyl.

2. The compound as recited in claim 1, wherein R$^1$ is F or CF$_3$, and R$^2$ is F.

3. The compound as recited in claim 1, wherein R$^3$ and R$^4$ are each methyl.

4. An electrolyte for at least one of a primary battery and a secondary battery, the electrolyte comprising the compound as recited in claim 1.

5. The electrolyte as recited in claim 4, wherein the compound is present in the electrolyte in a proportion of ≥1.5 wt.-% and/or in a proportion of ≤10.0 wt.-% based on a total weight of the electrolyte.

6. The electrolyte as recited in claim 4, wherein the compound is present in the electrolyte in a proportion of approximately 5 wt.-% based on a total weight of the electrolyte.

7. The electrolyte as recited in claim 4, wherein the electrolyte further comprises propylene carbonate, ethylene carbonate, diethyl carbonate, dimethyl carbonate, ethyl methyl carbonate, gamma-Butyrolactone, gamma-Valero-lactone, adiponitrile, glutaronitrile, acetonitrile, ethyl acetate, tetrahydrofuran, 2-methyltetrahydrofuran, dioxane, or a mixture thereof in a proportion of ≥30 wt.-% based on a total weight of the electrolyte.

8. The electrolyte as recited in claim 4, wherein the electrolyte further contains propylene carbonate in a proportion of ≥30 wt.-% based on a total weight of the electrolyte.

9. The electrolyte as recited in claim 4, wherein the electrolyte further comprises a conducting salt.

10. The electrolyte as recited in claim 9, wherein the conducting salt is a lithium conducting salt selected from LiPF$_6$, LiBF$_4$, LiAsF$_6$, LiSbF$_6$, lithium bisoxalatoborate, lithium difluorooxalatoborate, lithium salts of sulfonyl imides, LiClO$_4$, LiN(SO$_2$CF$_3$)$_2$, LiC(SO$_2$CF$_3$)$_3$, and LiSO$_3$CF$_3$.

11. A method for producing a compound with the general formula (I)

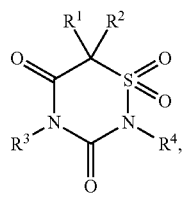

(I)

or a salt thereof, wherein,
R$^1$ and R$^2$, are, independently of each other, F or C$_n$F$_{2n+1}$ with n=1-10, and
R$^3$ and R$^4$ are, independently of each other, C$_1$-C$_{10}$-alkyl, the method comprising:
reacting a compound with the general formula (II)

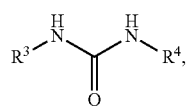

(II)

wherein,
R$^3$ and R$^4$ are, independently of each other, C$_1$-C$_{10}$-alkyl, with a compound with the general formula (III),

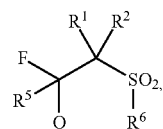

(III)

wherein, R$^1$ and R$^2$ are, independently of each other, F or C—F$_{2+1}$ with n=1-10, and
wherein,
R$^5$ is the O-atom on the same C-atom, and R$^6$ is F, or
R$^5$ is F, and R$^6$ is the O-atom bonded to the same C-atom to which R$^5$ is also bonded.

12. The method for producing as recited in claim 11, wherein the compound with the general formula (III) is a compound with the general formula (IIa)

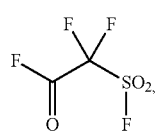

(IIIa)

or a compound with a compound with the general formula (IIIb)

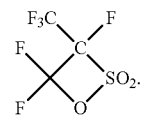

(IIIb)

13. The method for producing as recited in claim 12, wherein R$^3$ and R$^4$ are each methyl.

14. At least one of a primary battery, a secondary battery, a primary battery pack, and a secondary battery pack comprising the electrolyte as recited in claim 4.

15. At least one of an electric appliance and an electric vehicle comprising at least one of the primary battery, the secondary battery, the primary battery pack, and the secondary battery pack as recited in claim 14.

16. A method of using the compound as recited in claim 1 as an addition to at least one of a primary battery electrolyte and a secondary battery electrolyte, the method comprising:
providing the compound as recited in claim 1; and
using the compound as an addition in at least one of the primary battery electrolyte and the secondary battery electrolyte.

17. The method of using as recited in claim 16, wherein the compound is provided in the at least one of the primary battery electrolyte and the secondary battery electrolyte in a proportion of ≥1.5 wt.-% and/or in a proportion of ≤10.0 wt.-% based on a total weight of the at least one of the primary battery electrolyte and the secondary battery electrolyte.

18. The method of using as recited in claim 16, wherein the compound is provided in the at least one of the primary battery electrolyte and the secondary battery electrolyte in a proportion of approximately 5 wt.-% based on a total weight of the at least one of the primary battery electrolyte and the secondary battery electrolyte.

19. The method of using as recited in claim 16, further comprising,
providing propylene carbonate, ethylene carbonate, diethyl carbonate, dimethyl carbonate, ethyl methyl carbonate, gamma-Butyrolactone, gamma-Valerolactone, adiponitrile, glutaronitrile, acetonitrile, ethyl acetate, tetrahydrofuran, 2-methyltetrahydrofuran, dioxane, or mixtures thereof in a proportion of ≥30 wt.-% based on a total weight of the at least one of the primary battery electrolyte and the secondary battery electrolyte.

20. The method of using as recited in claim 16, further comprising,
providing a conducting salt.

21. The method of using as recited in claim 20, wherein the conducting salt is a lithium conducting salt selected from LiPF$_6$, LiBF$_4$, LiAsF$_6$, LiSbF$_6$, lithium bisoxalatoborate, lithium difluorooxalatoborate, lithium salts of sulfonyl imides, LiClO$_4$, LiN(SO$_2$CF$_3$)$_2$, LiC(SO$_2$CF$_3$)$_3$, and LiSO$_3$CF$_3$.

* * * * *